(12) United States Patent
Okumura (10) Patent No.: US 8,070,681 B2
(45) Date of Patent: Dec. 6, 2011

(54) ULTRASONIC PROBE AND ULTRASONIC DIAGNOSTIC APPARATUS

(75) Inventor: Yuji Okumura, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 1188 days.

(21) Appl. No.: 11/398,796

(22) Filed: Apr. 6, 2006

(65) Prior Publication Data
US 2006/0241475 A1 Oct. 26, 2006

(30) Foreign Application Priority Data
Apr. 7, 2005 (JP) .................................. 2005-111207

(51) Int. Cl.
*G01S 7/48* (2006.01)

(52) U.S. Cl. ........ 600/437; 600/407; 600/441; 600/443; 600/447; 600/449

(58) Field of Classification Search .................. 600/407, 600/437, 441, 443, 444, 447, 449, 459
See application file for complete search history.

(56) References Cited

U.S. PATENT DOCUMENTS

| 4,817,066 | A | * | 3/1989 | Takasugi et al. ............... 367/137 |
| 5,163,434 | A | * | 11/1992 | Kumazawa ..................... 600/455 |
| 5,520,187 | A | | 5/1996 | Snyder |
| 5,832,923 | A | | 11/1998 | Engeler et al. |
| 5,897,501 | A | | 4/1999 | Wildes et al. |
| 6,183,419 | B1 | | 2/2001 | Wildes |
| 6,759,888 | B1 | | 7/2004 | Wodnicki |
| 6,836,159 | B2 | | 12/2004 | Wodnicki |
| 6,868,729 | B2 | | 3/2005 | Amemiya |

FOREIGN PATENT DOCUMENTS
JP 2004-358105 12/2004
* cited by examiner

Primary Examiner — Tse Chen
Assistant Examiner — Mark Remaly
(74) Attorney, Agent, or Firm — Armstrong Teasdale LLP (57) ABSTRACT

It is intended to provide an ultrasonic probe permitting a reduction of a number of switching components while transmitting and receiving signals with the picture quality level held capable of being maintained. An ultrasonic the probe comprises transducers, transducer side cables which number is equal to a number of said transducers and are connected to the transducers, apparatus body side cables which number is less than a number of the transducer side signal lines and are connected to an apparatus body, switching units for switching connections of a transducer side cables of groups A and C which is connected to the apparatus body side cables of group D, and resistors provided between the transducer side cables of group B and the apparatus body side cables of group E.

14 Claims, 3 Drawing Sheets

ULTRASONIC PROBE AND ULTRASONIC DIAGNOSTIC APPARATUS

CROSS REFERENCE TO RELATED APPLICATIONS

This application claims the benefit of Japanese application No. 2005-111207 filed Apr. 7, 2005.

BACKGROUND OF THE INVENTION

The present invention relates to an ultrasonic probe and an ultrasonic diagnostic apparatus.

An ultrasonic diagnostic apparatus whose system has less number of channels than the number of transducer elements is known (e.g. JP-A No. 2004-358105). For instance in an electron scanning type ultrasonic diagnostic apparatus, since every transducer transmits and receives ultrasonic waves all the time, the number of channels on the system side can be less than the number of transducers. In such an ultrasonic diagnostic apparatus, by disposing multiplexer ICs between transducers and system channels for instance, transmission and reception with fewer system channels than the transducers is realized.

However, in such an ultrasonic apparatus, though a multiplexer is connected to every transducer, ON/OFF switching is not performed in every multiplexer. In an electron scanning system for instance, the multiplexer connected to the transducer arranged at the center of a probe may be used in a mode of being kept ON all the time. And since multiplexer ICs are generally expensive, the presence of unused multiplexers might invite an undue cost increase.

On the other hand, since multiplexer ICs also have resistance components such as ON resistors, indiscreet dispensation with a multiplexer IC used in a mode of being kept ON all the time would be detrimental to the uniformity of picture quality. For instance, dispensation with a multiplexer IC would invite an increased signal intensity due to a drop in resistance between the transducer and the system channel and accordingly partially greater brightness of the image.

SUMMARY OF THE INVENTION

The present invention is intended to provide an ultrasonic probe and an ultrasonic diagnostic apparatus permitting a reduction in the number of switching components while transmitting and receiving signals with the picture quality level being kept.

An ultrasonic probe according to a first aspect of the invention, comprising: a plurality of transducers for mutual conversion between ultrasonic waves and electric signals; a plurality of transducer side signal lines which number is equal to a number of said tranducers and are connected to said transducers; a plurality of apparatus body side signal lines which number is less than a number of said tranducers and are connected to said apparatus body; switching units for switching connections between the transducer signal lines included in a first group and the apparatus body side signal lines included in a second group, wherein said first group consists of a part of said transducer signal lines and said second group consists of a part of said apparatus body side signal lines which number is less than a number of the transducer side signal lines of the first group; and resistors provided between the transducer signal lines included in a third group and the apparatus body side signal lines included in a fourth group, wherein said third group consists of the other part of the transducers side signal lines and the fourth group consists of the apparatus body side signal lines which number is equal to a number of the transducer side signal lines in the third group.

Preferably, the resistances of the resistors may be equivalent to the values of the ON resistances of the switching units.

Preferably, electrostatic capacitance elements having electrostatic capacitances equivalent to the parasitic capacitances of the switching units on the transducer side and connected to the transducer side signal lines of the third group and a reference potential may be further provided.

Preferably, electrostatic capacitance elements having electrostatic capacitances equivalent to the parasitic capacitances of the switching units on the apparatus body side and connected to the apparatus body side signal lines of the fourth group and a reference potential may be further provided.

Preferably, resistors having resistances equivalent to the bleeder resistances provided on the transducer side of the switching units and connected to the transducer side signal lines of the third group and a reference potential may be further provided.

Preferably, resistors having resistances equivalent to the bleeder resistances provided on the apparatus body side of the switching units and connected to the apparatus body side signal lines of the fourth group and a reference potential may be further provided.

Preferably, the plurality of transducers are arrayed in a fixed direction; and the transducer side signal lines of the third group are connected to the arrayed transducer arranged at the center.

An ultrasonic probe according to a second aspect of the invention, comprising: a plurality of transducers which are arrayed in a fixed direction for mutual conversion between ultrasonic waves and electric signals; transducer side signal lines which number is equal to a number of said tranducers and are connected to said transducers; a plurality of apparatus body side signal lines which number is less than a number of said tranducers and are connected to said apparatus body and said transducer side signal lines; switching units for switching connections of the transducer signal lines included in side parts of the transducer signal lines connected to the arrayed transducers which are connected to the apparatus body side signal lines which number is smaller than the transducer side signal lines in the side parts; and connecting portions wherein the transducer side signal lines connected to the transducers in the center part of the arrayed transducers are directly connected to an equal number of the apparatus body side signal lines connected to the transducers in the center part of the arrayed transducers.

Preferably, the switching units include multiplexer ICs.

An ultrasonic diagnostic apparatus according to a third aspect of the invention comprises: a plurality of transducers for mutual conversion between ultrasonic waves and electric signals; a plurality of transducer side signal lines which number is equal to a number of said tranducers and are connected to each of said transducers; a plurality of apparatus body side signal lines which number is less than a number of said tranducers and are connected to said apparatus body and said transducer side signal lines; switching units for switching connections of the transducer signal lines included in a first group which is connected to the apparatus body side signal lines included in a second group, wherein said first group consists of a part of said transducer signal lines and said second group consists of said apparatus body side signal lines which number is less than a number of the transducer side signal lines of the first group; and resistors provided between the transducer signal lines included in a third group and the apparatus body side signal lines included in a fourth group, wherein said third group consists of the other part of the transducers side signal lines and said fourth group consists of the apparatus body side signal lines which number is equal to a number of the transducer side signal lines in the third group; and an apparatus body for generating images of the subject based on signals from said ultrasonic probe.

Preferably, the transducers are arrayed in a fixed direction; the apparatus body includes a control unit for controlling the switching units as to perform electron type scanning by sequentially switching driven transducers in the fixed direction; and the transducer side signal lines of the third group are connected to the arrayed transducers arranged at the center.

An ultrasonic diagnostic apparatus according to a fourth aspect of the invention comprises: a plurality of transducers which are arrayed in a fixed direction for mutual conversion between ultrasonic waves and electric signals; transducer side signal lines which number is equal to a number if said tranducers and are connected to said transducers; a plurality of apparatus body side signal lines which number is less than a number of said tranducers and are connected to said apparatus body and said transducer side signal lines; switching units for switching connections of the transducer signal lines included in side parts of the transducer signal lines connected to the arrayed transducers, which are connected to the apparatus body side signal lines which number is less than a number of the transducer side signal lines in the side parts; and connecting portions wherein the transducer side signal lines connected to the arrayed transducers in the center are directly connected to an equal number of the apparatus body side signal lines connected to the arrayed transducers in the center; and an apparatus body for generating images of the subject based on signals from said ultrasonic probe.

According to the invention, it is possible to reduce the number of switching components while maintaining the level of picture quality.

DETAILED DESCRIPTION OF THE INVENTION

Figure 1:
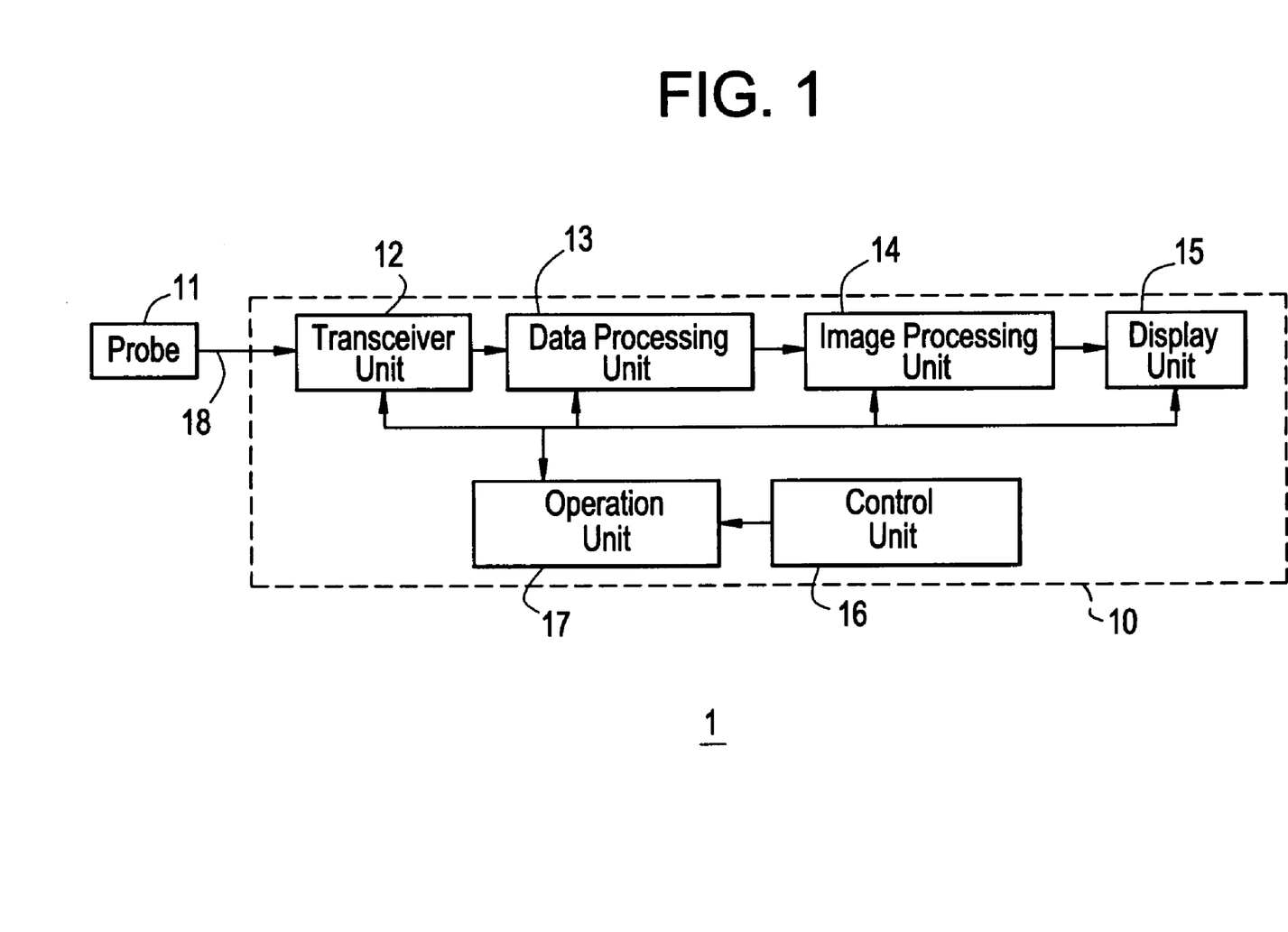
FIG. 1 is a block diagram showing the configuration of the ultrasonic diagnostic apparatus in a mode for carrying out the present invention.

FIG. 1 is a block diagram showing the overall configuration of an ultrasonic diagnostic apparatus 1 in a mode for carrying out the present invention. The ultrasonic diagnostic apparatus 1 is provided with a probe 11 which converts electric signals into a sound wave, transmits it, receives a sound wave reflected by a subject and converts it into electric signals, and an apparatus body 10 which generates or otherwise processes an image of the subject on the basis of the signals from the probe 11.

The apparatus body 10 is provided with a transceiver unit 12 which transmits and receives electric signals to and from the probe 11, a data processing unit 13 which executes the generation or the like of data for images on the basis of signals from the transceiver unit 12, an image processing unit 14 which outputs signals based on the data for images generated by the data processing unit 13, a display unit 15 which displays an ultrasonic image on the basis of the signals from the image processing unit 14, an operation unit 16 which accepts the user's input operations, and a control unit 17 which executes control of the units 12 through 15 on the basis of signals and the like from the operation unit 16.

The transceiver unit 12 is connected to the probe 11 via cables 18. The transceiver unit 12 gives drive signals to the ultrasonic probe 11 via the cables 18 in accordance with an instruction from the control unit 17. Further, the transceiver unit 12 receives echo signals from the probe 11 via the cables 18, subjects the received echo signals to amplification and other ways of processing and outputs them to the data processing unit 13.

The data processing unit 13, configured of a computer for instance, processes signals from the transceiver unit 12 in accordance with an instruction from the control unit 17, and generates data of an ultrasonic image of the subject. For instance, the data processing unit 13, after logarithmically amplifying the echo signals outputted by the transceiver unit 12, detects an envelope and generates image data in the B mode. Or, for example, the data processing unit 13 successively generates image data at prescribed timings and records the generated image data into a memory not shown. This makes possible three-dimensional moving image displaying (4D imaging) and the like.

The display processing unit 14, configured of a computer for instance, generates signals for having the display unit 15 display an ultrasonic image on the basis of image data outputted from the image processing unit 14 in accordance with an instruction from the control unit 17 or image data recorded in a memory not shown, and outputs them to the display unit 15.

The display unit 15, configured of a CRT display for instance, has a screen for displaying an ultrasonic image. The operation unit 16, provided with a keyboard and a pointing device for instance, outputs to the control unit 17 signals according to the input operation.

The control unit 17, configured of a computer for instance, is connected to the probe 11, the transceiver unit 12, the data processing unit 13, the image processing unit 14 and the display unit 15. The control unit 17 provides control signals to various units in accordance with operation signals from the operation unit 16 and controls their operations. The control unit 17, in order to perform electron type scanning with the probe 11, computes the drive timings and signal intensities of the transducers 31 (see FIG. 3) of the probe 11, and drives the probe 11 via the transceiver unit 12 in accordance with the computed drive timings and so forth.

Figure 2:
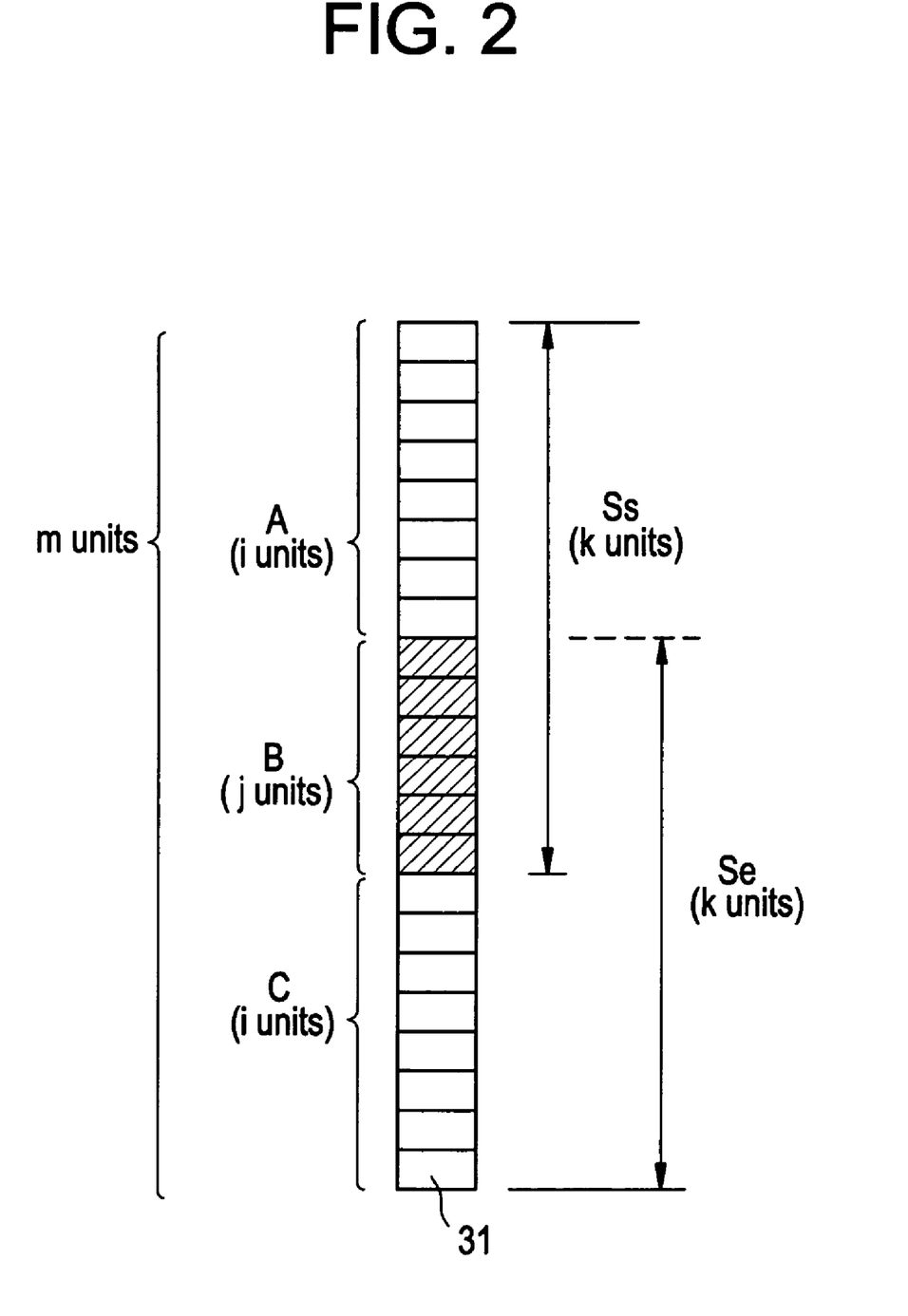
FIG. 2 is a diagram schematically showing the arrangement of the transducers of the probe of the ultrasonic diagnostic apparatus of FIG. 1.

FIG. 2 is a diagram schematically showing the arrangement and scanning method of the transducers 31 of the probe 11. The transducers 31, configured of a ceramic piezoelectric material or a macromolecular piezoelectric material, converts ultrasonic waves and electric signals between each other. The transducers 31 are arrayed in m units in a fixed direction (the vertical direction in the drawing).

In scanning, k transducers 31, fewer than the total m transducers 31, are driven in substantially the same period. And scanning is achieved by the shifting of the range of the driven transducers from range Ss to Se by one transducer at a time.

If k>m/2 here, the transducers 31 in group B positioned at the center in the direction of arrangement will be driven all the time. On the other hand, the transducers 31 in groups A and C positioned on the two sides of group B will be driven or not driven along with the progress of scanning.

Incidentally, where the numbers of transducers 31 in groups A and C are represented by i and that of transducers 31 in group B by j, j=2k−m and i=k−j will hold. For instance, k is set to be ⅔ of m, and i and j are respectively set to be ⅓ of m; more specifically, m is 192, k is 128 and i is 64 and j is 64.

Figure 3:
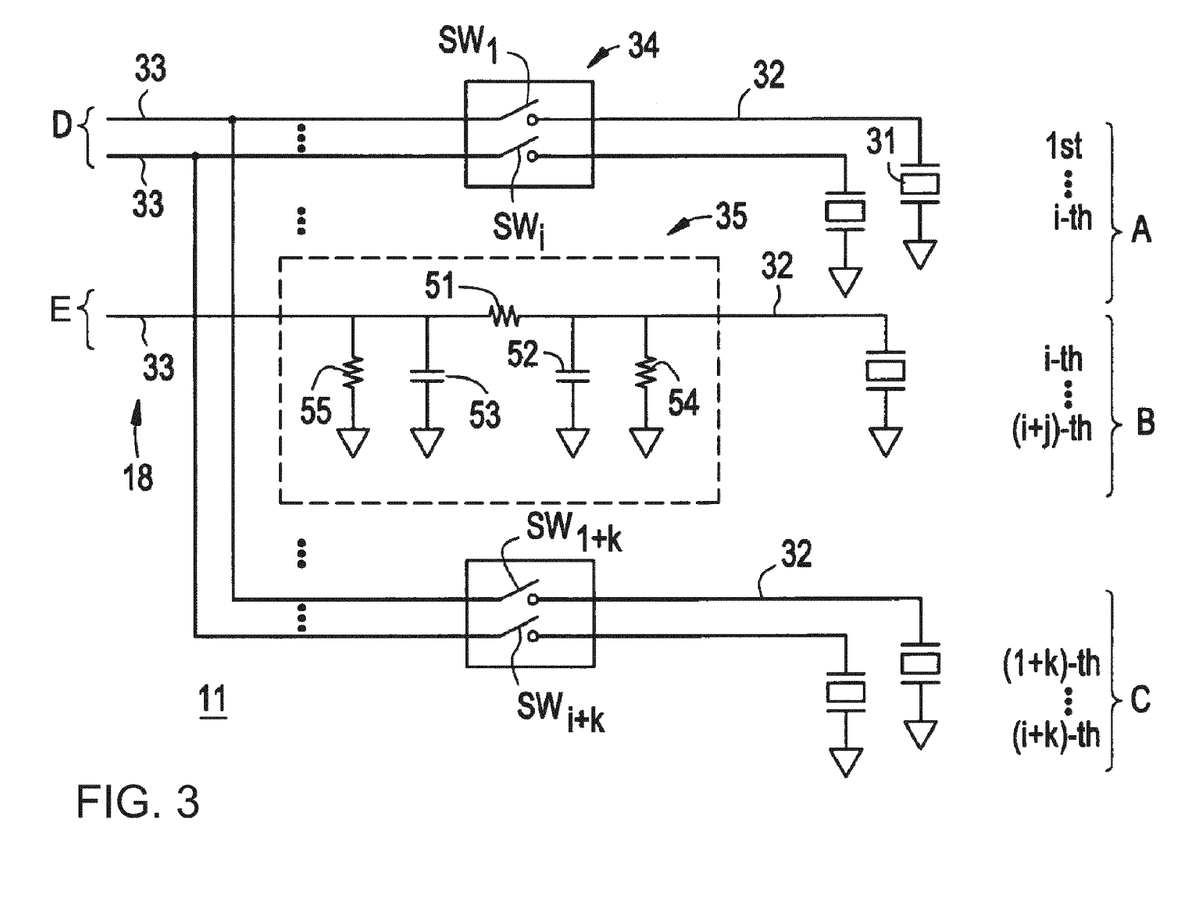
FIG. 3 is a circuit diagram schematically showing the configuration of the probe of the ultrasonic diagnostic apparatus of FIG. 1.

FIG. 3 is a circuit diagram schematically showing the configuration of the probe 11. The probe 11 is provided with transducer side cables 32 to be connected to the transducers 31 and apparatus body side cables 33 to be connected to the apparatus body 10.

The transducer side cables 32 and the apparatus body side cables 33 are configured of coaxial cables, for instance. The number of the transducer side cables 32 is the same as the number of the transducers 31. On the other hand, the number of the apparatus body side cables 33 is smaller than the number of the transducers 31. The number of the apparatus body side cables 33 is the same as, for instance, k which is the number of transducers 31 driven in substantially the same period (see FIG. 2). To add, the transducer side cables 32 and the apparatus body side cables 33 are included among the aforementioned cables 18 (see FIG. 1).

The transducer side cables 32 extending from the transducers 31 included in groups A and C (hereinafter sometimes referred to as the transducer side cables 32 of groups A and C) and the apparatus body side cables 33 of group D are connected or disconnected by switching units 34. The number of apparatus body side cables 33 included in group D is smaller than the numbers of the transducer side cables 32 included in groups A and C. For instance, number of apparatus body side cables 33 included in group D is ½ of the numbers of the transducer side cables 32 included in groups A and C. Incidentally, groups A and C constitute one example of first group and group D is an example of second group.

On the other hand, the transducer side cables 32 extending from the transducers 31 included in group B (hereinafter sometimes referred to as the transducer side cables 32 of group B) and the apparatus body side cables 33 of group E are connected to each other via connecting units 35. The number of apparatus body side cables 33 included in group E is the as the number of transducer side cables 32 included in group B. Incidentally, group B is one example of third group, and group E is one example of fourth group.

The switching units 34 switch over the connections between the transducer side cables 32 of groups A and C and the apparatus body side cables 33 of group D. The switchover will be adequate if the cables over which signals are communicated are changed, but is not limited to mechanical connection or disconnection between the cables 32 and the cables 33. Each switching unit 34 has a configuration of including a multiplexer IC for instance. The multiplexer IC is configured of a MOS FET for instance, and has two or more channels. As many multiplexer ICs are provided as the quotient of dividing the transducer side cables 32 of groups A and C by the number of channels of the multiplexer ICs. For example where the number of the transducer side cables 32 of groups A and C is 128, if the multiplexer ICs have two channels, 64 multiplexer ICs will be provided or if they have eight channels, 16 multiplexer ICs will be provided.

The multiplexers IC are caused by signal inputting by the control unit 17 (see FIG. 1) to the transducer 12 and the cable 18 to distribute signals from the apparatus body side cables 33 of group D of FIG. 3 to the transducer side cables 32 of groups A and C and a plurality of signals from the transducer side cables 32 of groups A and C to be selectively outputted to the apparatus body side cables 33 of group D. This results in switch-over of the connections between the transducer side cables 32 of groups A and C and the apparatus body side cables 33 of group D.

As many connecting units 35 as the transducer side cables 32 if group B are provided, each having a resistor 51, capacitors 52 and 53, and bleeder resistances 54 and 55.

The resistor 51 is connected to the transducer side cables 32 of group B and the apparatus body side cables 33 of group E. The resistance of the resistor 51 is equivalent to the ON resistances of the switching units 34. It is a resistance equivalent, for instance, to the resistance, when ON, from one of the terminals to which the transducer side cable 32 in a multiplexer IC is connected to another terminal to which an apparatus body side cable 33 is connected, and is about 20Ω for example.

The capacitor 52 is connected to the transducer side cables 32 and to reference electricity. The capacitor 52 has an electrostatic capacitance equivalent to the parasitic capacitance of the switching unit 34 on the transducer side, the so-called input capacitance. It has, for instance, an electrostatic capacitance equivalent to the electrostatic capacitance between one of the terminals to which the transducer side cable 32 in a multiplexer IC is connected and the reference potential, and has an electrostatic capacitance of about 40 pF for example.

The capacitor 53 is connected to the apparatus body side cables 33 and reference electricity. The capacitor 53 has an electrostatic capacitance equivalent to the parasitic capacitance of the switching units 34 on the apparatus body side, the so-called output capacitance. It has, for instance, an electrostatic capacitance equivalent to the electrostatic capacitance between one of the terminals to which the apparatus body side cable 33 in a multiplexer IC is connected and the reference potential, and has an electrostatic capacitance of about 40 pF for example.

The bleeder resistance 54 is connected to the transducer side cables 32 and reference electricity. The resistance of the bleeder resistance 54 is equivalent to that of a bleeder resistance provided on the transducer side of the switching unit 34. It is a resistance equivalent, for instance, to the resistance of a bleeder resistance provided on the side of one of the terminals to which the transducer side cable 32 in a multiplexer IC is connected, and is about 35 kΩ for instance.

The bleeder resistance 55 is connected to the apparatus body side cables 33 and reference electricity. The resistance of the bleeder resistance 55 is equivalent to that of a bleeder resistance provided on the apparatus body side of the switching unit 34. It is a resistance equivalent, for instance, to the resistance of a bleeder resistance provided on the side of a terminal to which the apparatus body side cable 33 in a multiplexer IC is connected, and is about 35 kΩ for instance.

To add, as the value of the ON resistance parasitic capacitance and the value of the bleeder resistance, the values indicated as respective standards by the manufacturer or distributor of the multiplexer ICs may be used, these values with prescribed corrections may be used, or values experimentally obtained by the manufacturer or distributor of the probe 11, the user or some other party may be used.

The operations by the probe 11 having the foregoing configuration will be described below.

Incidentally, the multiplexer IC is represented by an equivalent circuit in FIG. 3 to facilitate the description of the operations by the probe 11. Thus, the apparatus body side cable 33 is branched, and a plurality of switches SW to connect or disconnect the two cables to or from each other are represented by the switching units 34.

In the probe 11 shown in FIG. 3, the n-th ($1 \leqq n \leqq i$) transducer 31 in group A and the (n+k)-th transducer 31 in group C share one apparatus body side cable 33; for instance, the switching unit 34 is so controlled as to turn one of switches $SW_n$ and $SW_{n+k}$ on and the other off, transmission/reception over system channels which are smaller in number than the transducers 31 is realized. More specifically, it takes place as follows.

At the start of scanning, switches $SW_1$ through $SW_i$ on the group A are turned on and switches $SW_{1+k}$ through $SW_{i+k}$ on the group C side are turned off. This enables the transducers 31 of groups A and B to transmit and receive ultrasonic waves.

Next, the switch $SW_1$ is turned off and the switch $SW_{1+k}$ is turned on. This causes the range of the transducers 31 to be driven by one. Similarly, switches SW on the group A side until the switch $SW_i$ are turned off, and switches SW on the group C side until the switch $SW_{i+k}$ are turned on successively.

In the mode for carrying out the invention described above, since multiplexers IC corresponding constantly driven transducers are dispensed with and the resistors 51 having equivalent resistances to the multiplexer IC are provided, the phenomenon of partial brightening of the image due to a drop in resistance between the transducers 31 of group B and the apparatus body 10 can be prevented while obtaining various benefits including the cost saving and the facilitation of control due to the dispensation with multiplexers IC.

By providing the capacitors 52 and 53 equivalent to the parasitic capacitances of the multiplexers IC and thereby lowering the band of signals in the detection system of group B to the bands in the detection systems of groups A and C, partial brightening of the image can be prevented.

By providing the bleeder resistances 54 and 55 equivalent to the bleeder resistances of the multiplexers IC and equalizing the quantity of noise getting mixed into signals in the detection system of group B to the quantities of noise getting mixed into signals in the detection systems of groups A and C group, the image quality can be uniformized.

The present invention is not limited to the above-described mode for implementation, but may be carried out in various other modes.

The ultrasonic diagnostic apparatus is not limited to an electron scanning type apparatus. It only needs to have a smaller number of channels in the apparatus body than the number of transducer elements.

The resistors provided between the transducers and the apparatus body need not be equivalent to the ON resistance of the switching units. It is because, if the resistance is made higher, if only slightly, by providing resistors between the transducers and the apparatus body than where only the switching units are dispensed with, the image quality can be considered improved. Incidentally, though every electronic component has a resistance, whether or not the component can be regarded as a resistor according to the invention can be determined whether or not the resistor is provided only on a signal line on which no switching unit is proposed. And preferably, it is desirable to provide resistors whose resistances are 50% or more of the ON resistance.

Depending on the position of the transducer for which the switching unit is dispensed with, no resistor needs to be provided between the transducer and the apparatus body. For instance where transducers are arrayed in a certain direction and the switching unit matching the transducer arranged at their center is to be dispensed with, no resistor needs to be provided between the transducer and the apparatus body. Where a subject is to be diagnosed, since scanning is generally so performed as to position the target region at the center of the image, the transducers on the central side meet the target region. A further reason is that, if the quality of the image becomes uneven, improvement in the image quality in the target region would pose no serious problem, or rather be preferable depending on the situation of use. To add, cases in which switching units are dispensed with and transducer side signal lines and the apparatus body side signal lines are directly connected to each other include a case in which the transducer side signal line and the apparatus body side signal line are composed of a single signal line.

Where switching units may be dispensed with, at least one of the static capacitance elements and bleeder resistances which are provided instead of them can be dispensed with. The reason is that, where switching units are dispensed with, what most affects the image quality is the ON resistance, and if resistors are provided between the transducers and the apparatus body, the image quality can be uniformized. Another reason is that bleeder resistances are not always provided in switching units.

Further, these electrostatic capacitance elements and bleeder resistances need not be equivalent to the parasitic capacitances or the bleeder resistances of switching units. The reason is that, if the presence of those electrostatic capacitance elements and bleeder resistances brings the electrostatic capacitances and the like closer to parasitic capacitances or the like of the switching units if only slightly than where only the switching units are dispensed with, the image quality can be considered uniformized. However, it is desirable for the electrostatic capacitance elements to have 50% or more of the parasitic input capacitances or the parasitic output capacitances of the switching units and have 50% to 150% of the bleeder resistances on the input side or the output side of the switching units.

The transducer side signal lines need not be directly connected to the transducers. It will be sufficient if signals from the transducers or signals to the transducers can be communicated and as many of them as the transducers are provided. For instance, they may be connected to the transducers via other cables or the like, namely indirectly.

Similarly, the apparatus body side signal lines need not be directly connected to the apparatus body. It will be sufficient if signals from the apparatus body or signals to the apparatus body can be communicated and their number is smaller than that of transducers and, for instance, FPC or the like may intervene between the apparatus body side signal lines and the apparatus body. Also, it is appropriate for the number of apparatus body side signal lines to be smaller than the number of transducer side signal lines, but their number is not limited to the same number as that of transducers driven in substantially the same period.

The connecting units in which switching units are dispensed with may as well be provided with inductors equivalent in inductance to the inductances of the switching units.

The invention claimed is:

1. An ultrasonic probe comprising:
a plurality of transducers for mutual conversion between ultrasonic waves and electric signals, a subset of said plurality of transducers configured to be driven in a same period during a scanning process, said subset including a number of transducers less than a total number of transducers of said plurality of transducers;
a plurality of transducer side signal lines connected to said plurality of transducers, a number of said plurality of transducer side signal lines equal to a number of said plurality of transducers;
a plurality of apparatus body side signal lines connected to an apparatus body, a number of said plurality of apparatus body side signal lines equal to the number of transducers in said subset of said plurality of transducers;
a first set of switching units for switching connections between transducer side signal lines of said plurality of transducer side signal lines included in a first group and apparatus body side signal lines of said plurality of apparatus body side signal lines included in a second group, wherein said first group comprises a first part of said plurality of transducer side signal lines and said second group comprises a first part of said plurality of apparatus body side signal lines, a number of said first part of said plurality of apparatus body side signal lines less than a number of said plurality of transducer side signal lines of said first group, each switching unit in the first set of switching units comprising a multiplexer configured to distribute signals from the apparatus body side signal lines in the second group to the transducer side signal lines in the first group and distribute signals from the transducer side signal lines in the first group to the apparatus body side signal lines in the second group;

a plurality of connecting units comprising a capacitor, each of the plurality of connecting units provided between one of said plurality of transducer side signal lines included in a third group and a corresponding one of said plurality of apparatus body side signal lines included in a fourth group, wherein said third group comprises a second part of said plurality of transducer side signal lines and said fourth group comprises a second part of said plurality of apparatus body side signal lines equal to a number of the transducer side signal lines in the third group, each said connecting unit not including a multiplexer, wherein each of said plurality of connecting units is not connected to a switching unit; and a second set of switching units for switching connections between transducer side signal lines of said plurality of transducer side signal lines included in a fifth group and apparatus body side signal lines of said plurality of apparatus body side signal lines included in a sixth group, wherein said fifth group comprises a third part of said plurality of transducer side signal lines and said sixth group comprises a third part of said plurality of apparatus body side signal lines, a number of said third part of said plurality of apparatus body side signal lines less than a number of said plurality of transducer side signal lines of said fifth group, each switching unit in the second set of switching units comprising a multiplexer configured to distribute signals from the apparatus body side signal lines in the fifth group to the transducer side signal lines in the sixth group and distribute signals from the transducer side signal lines in the sixth group to the apparatus body side signals in the fifth group; and wherein each multiplexer is defined by a parasitic capacitance; and wherein each capacitor of the plurality of connecting units has electrostatic capacitance elements having electrostatic capacitances equivalent to the parasitic capacitances of each multiplexer.

2. The ultrasonic probe according to claim 1, wherein each multiplexer is defined by resistance and a bleeder resistance.

3. The ultrasonic probe according to claim 2, wherein each of the plurality of connector units comprises one or more resistors having resistances equivalent to the bleeder resistances of each multiplexer.

4. The ultrasonic probe according to claim 1, wherein each of the plurality of connector units comprises one or more resistors having a resistance equivalent to a value of an ON resistance of each multiplexer.

5. The ultrasonic probe according to claim 1, wherein said plurality of transducers are arrayed in a fixed direction, and said one transducer side signal line of said third group is connected to an arrayed transducer arranged at a center.

6. An ultrasonic probe comprising:

a plurality of transducers arrayed in a fixed direction for mutual conversion between ultrasonic waves and electric signals, a subset of said plurality of transducers configured to be driven in a same period during a scanning process, said subset including a number of transducers less than a total number of transducers of said plurality of transducers;

a plurality of transducer side signal lines connected to said plurality of transducers, a number of said transducer side signal lines equal to a number of said plurality of transducers;

apparatus body side signal lines connected to an apparatus body and said transducer side signal lines, a number of said apparatus body side signal lines equal to the number of transducers in said subset of said plurality of transducers;

a first set of switching units for switching connections of a first group of transducer side signal lines included in side parts of said plurality of transducer side signal lines connected to said plurality of arrayed transducers connected to a first group of said apparatus body side signal lines, a number of said apparatus body side signal lines in the first group of said apparatus body side signal lines being less than a number of transducer side signal lines in the first group of said transducer side signal lines in the side parts, each switching unit in the first set of switching units comprising a multiplexer configured to distribute signals from the apparatus body side signal lines in the first group to the transducer side signal lines in the first group and distribute signals from the transducer side signal lines in the first group to the apparatus body side signal lines in the first group;

a connecting unit comprising a capacitor, wherein transducer side signal lines connected to transducers in a center part of said arrayed transducers are directly connected to an equal number of apparatus body side signal lines connected to transducers in the center part of said arrayed transducers via said connecting unit, said connecting unit not including a multiplexer, and wherein said connecting unit is not connected to a switching unit; and a second set of switching units for switching connections of a second group of transducer side signal lines included in side parts of said plurality of transducer side signal lines connected to said plurality of arrayed transducers connected to a second group of said apparatus body side signal lines, a number of said apparatus body side signal lines in the second group of said apparatus body side signal lines being less than a number of transducer side signal lines in the second group of said transducer side signal lines in the side parts, each switching unit in the second set of switching units comprising a multiplexer configured to distribute signals from the apparatus body side signal lines in the second group to the transducer side signal lines in the second group and distribute signals from the transducer side signal lines in the second group to the apparatus body side signal lines in the second group; and wherein each multiplexer is defined by a parasitic capacitance; and wherein each capacitor of the plurality of connecting units has electrostatic capacitance elements having electrostatic capacitances equivalent to the parasitic capacitances of each multiplexer.

7. The ultrasonic probe according to claim 1, wherein the multiplexers are multiplexer ICs.

8. An ultrasonic diagnostic apparatus comprising:
an ultrasonic probe for irradiating a subject with an ultrasonic wave and for receiving a reflected ultrasonic wave, said ultrasonic probe comprising:
- a plurality of transducers for mutual conversion between ultrasonic waves and electric signals, a subset of said plurality of transducers configured to be driven in a same period during a scanning process, said subset including a number of transducers less than a total number of transducers of said plurality of transducers;
- a plurality of transducer side signal lines connected to each of said plurality of transducers, a number of said plurality of transducer side signal lines equal to a number of said plurality of transducers;
- a plurality of apparatus body side signal lines connected to an apparatus body and said plurality of transducer side signal lines, a number of said plurality of apparatus body side signal lines equal to the number of transducers in said subset of said plurality of transducers;
- a first set of switching units for switching connections of transducer side signal lines included in a first group connected to apparatus body side signal lines included in a second group, wherein said first group comprises a first part of said plurality of transducer side signal lines and said second group comprises said a first part of said plurality of apparatus body side signal lines, a number of said first part of said plurality of apparatus body side signal lines less than a number of said first part of said plurality of transducer side signal lines of said first group, each switching unit in the first set of switching units comprising a multiplexer configured to distribute signals from the apparatus body side signal lines in the first group to the transducer side signal lines in the second group and distribute signals from the transducer side signal lines in the first group to the apparatus body side signal lines in the second group;
- a plurality of connecting units comprising a capacitor, each of the plurality of connecting units provided between one of said plurality of transducer side signal lines included in a third group and a corresponding one of said plurality of apparatus body side signal lines included in a fourth group, wherein said third group comprises a second part of said plurality of transducer side signal lines and said fourth group comprises a second part of said plurality of apparatus body side signal lines equal to a number of the transducer side signal lines in the third group, said connecting unit not including a multiplexer, wherein each of said plurality of connecting units is not connected to a switching unit;
- a second set of switching units for switching connections between transducer side signal lines of said plurality of transducer side signal lines included in a fifth group and apparatus body side signal lines of said plurality of apparatus body side signal lines included in a sixth group, wherein said fifth group comprises a third part of said plurality of transducer side signal lines and said sixth group comprises a third part of said plurality of apparatus body side signal lines, a number of said third part of said plurality of apparatus body side signal lines less than a number of said plurality of transducer side signal lines of said fifth group, each switching unit in the second set of switching units comprising a multiplexer configured to distribute signals from the apparatus body side signal lines in the fifth group to the transducer side signal lines in the sixth group and distribute signals from the transducer side signal lines in the sixth group to the apparatus body side signal lines in the fifth group; and
an apparatus body for generating images of the subject based on signals from said ultrasonic probe; and
wherein each multiplexer is defined by a parasitic capacitance; and
wherein each capacitor of the plurality of connecting units has electrostatic capacitance elements having electrostatic capacitances equivalent to the parasitic capacitances of each multiplexer.

9. The ultrasonic diagnostic apparatus according to claim 8, wherein:
said plurality of transducers are arrayed in a fixed direction;
said apparatus body includes a control unit for controlling each switching unit so as to perform electron type scanning by sequentially switching driven transducers in said fixed direction; and
said one transducer side signal line of said third group is connected to one of said arrayed transducers, said one arrayed transducer arranged at a center.

10. An ultrasonic diagnostic apparatus comprising:
an ultrasonic probe for irradiating a subject with an ultrasonic wave and for receiving a reflected ultrasonic wave, said ultrasonic probe comprising:
- a plurality of transducers arrayed in a fixed direction for mutual conversion between ultrasonic waves and electric signals, a subset of said plurality of transducers configured to be driven in a same period during a scanning process, said subset including a number of transducers less than a total number of transducers of said plurality of transducers;
- a plurality of transducer side signal lines connected to said plurality of transducers, a number of said transducer side signal lines equal to a number of said plurality of transducers;
- apparatus body side signal lines connected to an apparatus body and said transducer side signal lines, a number of said apparatus body side signal lines less than equal to the number of transducers in said subset of said plurality of transducers;
- a first set of switching units for switching connections of a first group of transducer side signal lines included in side parts of said plurality of transducer side signal lines connected to said plurality of arrayed transducers connected to a first group of said apparatus body side signal lines, a number of said apparatus body side signal lines in the first group of said apparatus body side signal lines being less than a number of transducer side signal lines in the first group of said transducer side signal lines in the side parts, each switching unit in the first set of switching units comprising a multiplexer configured to distribute signals from the apparatus body side signal lines in the first group to the transducer side signal lines in the first group and distribute signals from the transducer side signal lines in the first group to the apparatus body side signal lines in the first group;
- a connecting unit comprising a capacitor, wherein transducer side signal lines connected to arrayed transducers in a center are directly connected to an equal number of apparatus body side signal lines connected to said arrayed transducers in the center via said connecting unit, said connecting unit not including a multiplexer, and wherein said connecting unit is not connected to a switching unit;
- a second set of switching units for switching connections of a second group of transducer side signal lines included in side parts of said plurality of transducer side signal lines connected to said plurality of arrayed transducers connected to a second group of said apparatus body side signal lines, a number of said apparatus body side signal lines in the second group of said apparatus body side signal lines being less than a number of transducer side signal lines in the second group of said transducer side signal lines in the side parts, each switching unit in the second set of switching units comprising a multiplexer configured to distribute signals from the apparatus body side signal lines in the second group to the transducer side signal lines in the second group and distribute signals from the transducer side signal lines in the second group to the apparatus body side signal lines in the second group; and an apparatus body for generating images of the subject based on signals from said ultrasonic probe; and wherein each multiplexer is defined by a parasitic capacitance; and wherein each capacitor of the plurality of connecting units has electrostatic capacitance elements having electrostatic capacitances equivalent to the parasitic capacitances of each multiplexer.

11. The ultrasonic probe according to claim 6, wherein said connecting unit comprises at least one of a resistor, and a plurality of bleeder resistances.

12. The ultrasonic probe according to claim 8, wherein said connecting unit comprises at least one of a resistor and a plurality of bleeder resistances.

13. The ultrasonic probe according to claim 10, wherein said connecting unit comprises at least one of a resistor, and a plurality of bleeder resistances.

14. The ultrasonic probe according to claim 1, wherein said subset of said plurality of transducers are driven during the entire scanning process, and wherein a remainder of transducers of said plurality of transducers not in said subset of said plurality of transducers are driven or not driven based on the progress of the scanning process.

* * * * *

UNITED STATES PATENT AND TRADEMARK OFFICE
CERTIFICATE OF CORRECTION

PATENT NO. : 8,070,681 B2
APPLICATION NO. : 11/398796
DATED : December 6, 2011
INVENTOR(S) : Okumura Page 1 of 1

It is certified that error appears in the above-identified patent and that said Letters Patent is hereby corrected as shown below:

In Column 1, Line 53, delete "tranducers" and insert. -- transducers --, therefor.

In Column 1, Line 55, delete "tranducers" and insert -- transducers --, therefor.

In Column 2, Line 33, delete "tranducers" and insert -- transducers --, therefor.

In Column 2, Line 36, delete "tranducers" and insert -- transducers --, therefor.

In Column 2, Line 53, delete "tranducers" and insert -- transducers --, therefor.

In Column 2, Line 56, delete "tranducers" and insert -- transducers --, therefor.

In Column 3, Line 17, delete "tranducers" and insert -- transducers --, therefor.

In Column 3, Line 19, delete "tranducers" and insert -- transducers --, therefor.

In Column 9, Line 43, in Claim 1, delete "signals" and insert -- signal lines --, therefor.

In Column 14, Line 4, in Claim 11, delete "resistor," and insert -- resistor --, therefor.

In Column 14, Line 10, in Claim 13, delete "resistor," and insert -- resistor --, therefor.

Signed and Sealed this
Tenth Day of April, 2012

David J. Kappos
*Director of the United States Patent and Trademark Office*